(12) United States Patent
Nichinonni

(10) Patent No.: US 6,500,003 B2
(45) Date of Patent: Dec. 31, 2002

(54) DENTAL IMPLANT ABUTMENT

(75) Inventor: Gianni Nichinonni, 59 Stanford Rd., Salisbury Heights, Adelaide S.A. 5109 (AU)

(73) Assignee: Gianni Nichinonni, Adelaide (AU)

( * ) Notice: Subject to any disclaimer, the term of this patent is extended or adjusted under 35 U.S.C. 154(b) by 0 days.

(21) Appl. No.: 09/882,262

(22) Filed: Jun. 14, 2001

(65) Prior Publication Data

US 2001/0053512 A1 Dec. 20, 2001

(30) Foreign Application Priority Data

Jun. 16, 2000 (AU) .............................. PQ8179

(51) Int. Cl.⁷ .................................. A61C 8/00
(52) U.S. Cl. ...................................... 433/173
(58) Field of Search ................ 433/172, 173, 433/174, 175, 176

(56) References Cited

U.S. PATENT DOCUMENTS

| | | | |
|---|---|---|---|
| 4,793,808 A | 12/1988 | Kirsch | 433/173 |
| 4,832,601 A | 5/1989 | Linden | 433/173 |
| 4,850,870 A | 7/1989 | Lazzara et al. | 433/174 |
| 5,281,140 A | 1/1994 | Niznick | 433/173 |
| 5,302,125 A | 4/1994 | Kownachi et al. | 433/172 |
| 5,376,004 A | 12/1994 | Mena | 433/173 |
| 5,527,182 A | 6/1996 | Willoughby | 433/172 |
| 5,599,185 A | 2/1997 | Greenberg | 433/173 |
| 5,662,473 A | 9/1997 | Rassoli et al. | 433/172 |
| 5,662,475 A | 9/1997 | Mena | 433/172 |
| 5,873,721 A | 2/1999 | Willoughby | 433/173 |
| 5,890,902 A | 4/1999 | Sapian | 433/173 |
| 5,947,733 A | 9/1999 | Sutter et al. | 433/173 |
| 6,126,445 A | 10/2000 | Willoughby | 433/172 |

FOREIGN PATENT DOCUMENTS

| | | |
|---|---|---|
| DE | 2704390 A1 | 8/1978 |
| EP | 0230678 A1 | 8/1987 |
| JP | 63139541 | 6/1988 |
| WO | WO99/16293 | 4/1999 |
| WO | WO00/28914 | 5/2000 |

OTHER PUBLICATIONS

International Search Report of International App. No. PCT/AU01/00716.
Abstract of DE 2704390 A1, Derwent WPI, Jun. 14, 2001.
Bibliography and abstract of JP 63139541.

*Primary Examiner*—Cary E. O'Connor
(74) *Attorney, Agent, or Firm*—Matthew J. Russo; Kenneth E. Horton; Rader, Fishman & Grauer PLLC

(57) ABSTRACT

An abutment for securing a dental prosthesis to an implant fixture is disclosed. The abutment includes a base and an attachable coping. The attachable coping carries the dental prosthesis and is mounted on the base of the abutment using a ball-and-socket joint, which permits the dental prosthesis to be easily and accurately aligned with adjacent teeth, implant fixtures or other prostheses. A connector inserted through an aperture in the base of the abutment secures the abutment and the prosthesis to the implant fixture.

9 Claims, 4 Drawing Sheets

DENTAL IMPLANT ABUTMENT

CROSS-REFERENCE TO RELATED APPLICATION

The present application claims priority to Australian Provisional Patent Application No. PQ 8179, filed Jun. 16, 2000.

TECHNICAL FIELD

The present invention relates to dental implants, and more particularly, to an abutment used to secure a dental prosthesis to an implant fixture.

BACKGROUND OF THE INVENTION

A dental implant assembly is a device that is surgically attached to a patient's jawbone to replace one or more missing teeth. A typical dental implant includes an implant fixture that an oral surgeon inserts into the jawbone, and a prosthesis, which replaces the crown portion of a missing tooth. Currently, the most prevalent type of dental implant fixture is a root-form implant. As its name suggests, the root-form implant has an elongated shape reminiscent of the root portion of a tooth. Much like roots of natural teeth, the root-form implant penetrates the gum and anchors the prosthesis to the jawbone.

The dental implant assembly also includes an abutment, which provides an interface or transition between the implant fixture and the prosthesis. Conventional abutments typically include a substantially axisymmetric base portion, which fits into a hole formed in the implant fixture, and a conical neck portion, which projects outward from the base portion of the abutment. Besides securing the prosthesis to the implant fixture, the abutment also compensates—with varying success—for any misalignment between the prosthesis and adjacent teeth. Misalignment can arise, for example, when the implant fixture has an orientation with respect to the gum surface that is substantially different than the adjacent teeth.

Implant assemblies employ angled abutments, as opposed to straight abutments, to account for any misalignment. Straight and angled abutments have neck portions that project outward from their base portions in directions that are, respectively, substantially parallel or non-parallel to the symmetry axes of their corresponding base portions. Therefore, if the direction or orientation of the neck portion of the abutment is represented by a longitudinal axis that intersects the symmetry axis of the base portion (or implant fixture), the resulting orientation angle is about zero for straight abutments. In contrast, an angled abutment exhibits a non-zero orientation angle. For a discussion of straight and angled abutments, see U.S. Pat. No. 5,947,733 issued to Franz Sutter et al., which is herein incorporated by reference in its entirety for all purposes.

Though widely accepted by dental practitioners, dental implants generally, and root-form implants in particular, are not without problems. For example, the neck portions of commercially available angled abutments have fixed angular displacements with respect to their base portions, which limits their usefulness. Once a patient has been fitted with an implant fixture, the dental practitioner must order an abutment having the requisite orientation angle to ensure proper alignment of the prosthesis. However, since only discrete orientation angles are available, it is often necessary to modify the abutment to achieve the requisite angular orientation, which can be a labor intensive and costly process. In some cases the necessary orientation angle may be significantly greater than what is commercially available, making it difficult to attain acceptable alignment of the prosthesis.

Dental implants having adjustable orientation angles are known, but none appear to have achieved widespread use because of design deficiencies. See, for example, U.S. Pat. No. 5,890,902 issued to Sapian; U.S. Pat. No. 5,662,475 issued to Mena; U.S. Pat. No. 5,599,185 issued to Greenburg; U.S. Pat. No. 5,302,125 issued to Kownacki et al.; U.S. Pat. No. 4,793,808 issued to Kirsch; and U.S. Pat. No. 4,832,601 issued to Linden, which are herein incorporated by reference in their entirety for all purposes. Most of the disclosed implants are limited to modest orientation angles of about twenty-five degrees or less, and many do not readily permit removal of the prosthesis following installation. Some of the disclosed implants also fail to provide a smooth transition between the prosthesis and the implant fixture, which results in poor soft tissue adaptation. To ensure accurate alignment of the prosthesis with adjacent teeth, current practice provides for fabricating an abutment and prosthesis from a cast of the patient's mouth following insertion of the implant fixture. Some of the disclosed designs, however, do not include a mechanism for attaching the prosthesis to the abutment prior to installation, and therefore cannot take advantage of using a laboratory cast, if desired.

The present invention is directed to overcoming, or at least reducing the effects of, one or more of the problems described above.

SUMMARY OF THE INVENTION

The present invention provides a dental implant abutment incorporating a ball-and-socket joint, which can be constructed from standard elements to reduce costs. The abutment allows one to adjust the orientation angle of an attached prosthesis over a continuous and wide range of values (fifty degrees or more) before fixing the desired angular orientation. The abutment readily permits removal of the prosthesis following installation and provides a smooth transition between the prosthesis and the implant fixture, which results in good soft tissue adaptation. The claimed invention also allows for accurate transfer of the abutment from the laboratory cast to the jawbone.

Thus, one aspect of the present invention provides an assembly for securing a permanent prosthesis to a root-form implant fixture. The implant fixture has a head portion, an adjoining root portion, and a hole extending from the head portion into the root portion of the implant fixture. The claimed assembly includes an abutment, which comprises a base and an attachable coping. The base has a first surface that is complementary to the head portion of the implant fixture, a second surface having a shape that approximates a section of a sphere, and a third surface that defines an aperture extending between the first and second surfaces of the base. The attachable coping has an exterior surface for receiving the permanent prosthesis, first and second openings in the exterior surface, and an interior surface that defines a cavity connecting the first and second openings. A portion of the interior surface of the attachable coping that is located adjacent to the first opening in the exterior surface is shaped to slidably engage the second surface of the base so that the attachable coping can be joined to the base at a desired angular orientation.

Another aspect of the present invention provides a connector for securing the abutment to the implant fixture. The connector has a head portion and a shaft portion adjoining the head portion. The head portion of the connector has a lateral surface configured to engage the third surface of the base, and the shaft portion of the connector has external threads adapted to engage internal threads in the hole in the implant fixture. During installation, the first surface of the base of the abutment is disposed on the head portion of the implant fixture so that the respective aperture and hole of the base and the implant fixture are substantially aligned. The connector is placed in the aperture so that rotating the head of the connector using a tool inserted through the second opening in the exterior surface of the attachable coping drives the connector into the hole in the implant fixture, thereby securing the abutment to the implant fixture.

DETAILED DESCRIPTION

Figure 1:
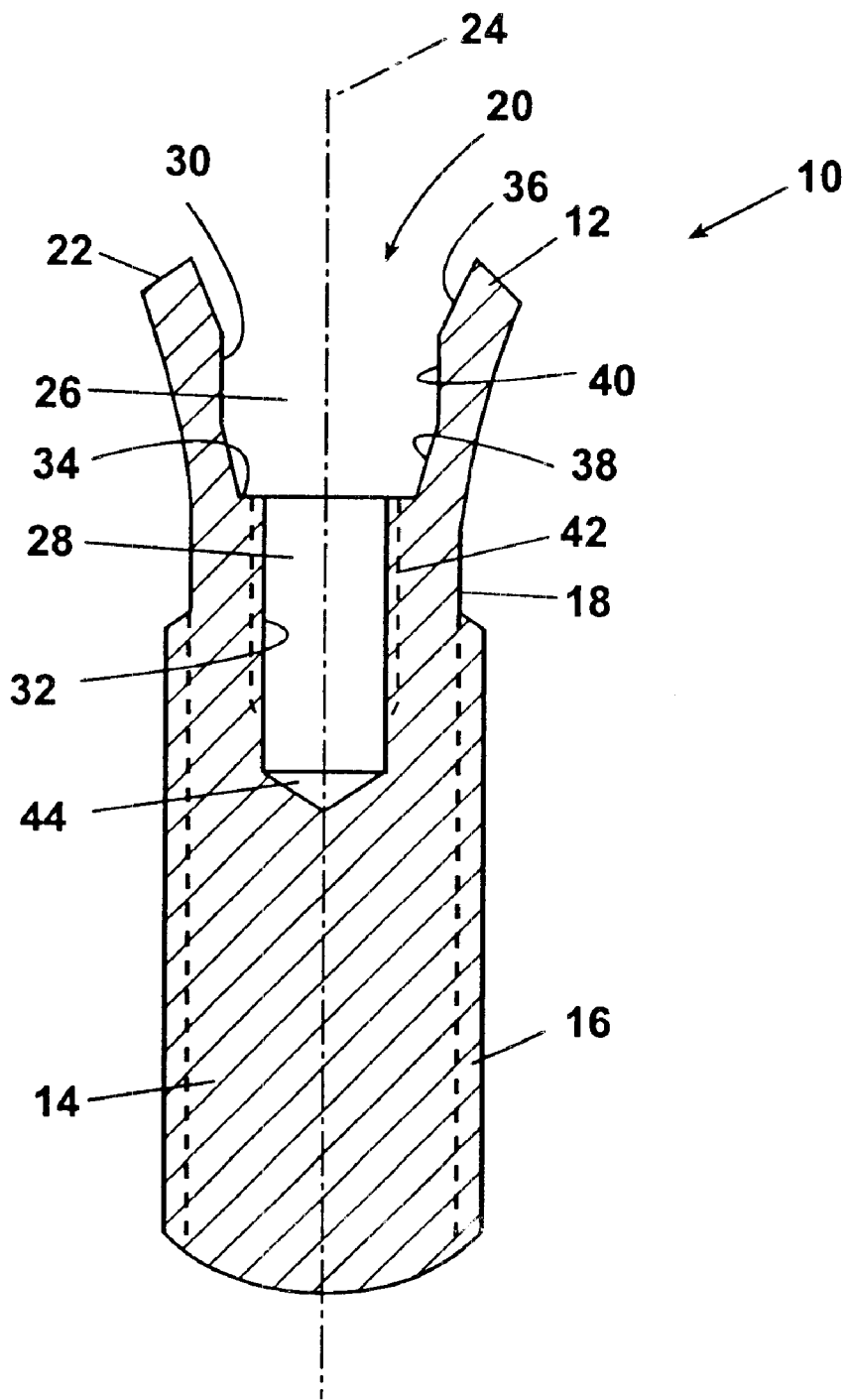
FIG. 1 shows a cross-sectional side view of one embodiment of an implant fixture.

FIG. 1 shows a cross-sectional side view of one embodiment of an implant fixture 10, which a dental practitioner inserts into a patient's jawbone. The implant fixture 10 is a root-form implant fixture and includes a head portion 12 and an adjoining root portion 14. The implant fixture 10 has a generally cylindrical shape and has external threads 16 formed along a section of an exterior surface 18 of the elongated root portion 14. The external threads 18 help stabilize the implant fixture 10 in the patient's jawbone during healing, but other embodiments may employ grooves, lateral holes, and the like to minimize rotation. The exterior surface 18 may be machined smooth, plasma sprayed to increase surface area, or coated with hydroxylapatite to promote fusion to the jawbone (osseointegration). The implant fixture 10 can be made of any material having the requisite mechanical strength and the ability to integrate into the jawbone. Useful materials include commercially pure titanium.

As shown in FIG. 1, the implant fixture 10 includes a longitudinal bore or hole 20, which extends from an upper exterior surface 22 of the head portion 12 into the elongated root portion 14 of the implant fixture 10. The hole 20, which has a centerline substantially coincident with a symmetry axis 24 of the implant fixture 10, includes an upper cavity 26, which is adapted to receive an abutment, and a comparatively narrower lower cavity 28, which is adapted to receive a connector. The upper 26 and lower 28 cavities are defined, respectively, by first 30 and second 32 lateral surfaces separated by an annular surface 34. The first lateral surface 30 includes a pair 36, 38 of inverted conical surfaces, and an intermediate cylindrical surface 40, but other embodiments may comprise a single inverted conical surface. The second lateral surface 32 has a cylindrical shape, and includes internal threads 42 that extend from the annular surface 34 to a region adjacent to the bottom 44 of the hole 20.

Figure 2:
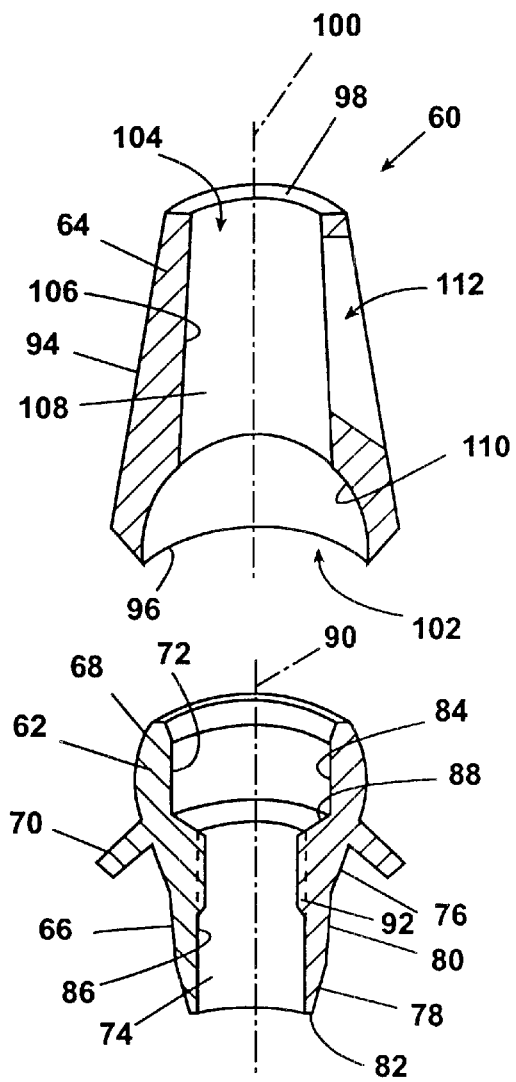
FIG. 2 shows an exploded, partial cross-sectional side view of an abutment adapted for use with the implant fixture shown in FIG. 1.

FIG. 2 shows an exploded, partial cross-sectional side view of an abutment 60, which is adapted for use with the implant fixture 10 shown in FIG. 1. The abutment 60, which secures a prosthesis (crown, bridge, etc.) to the implant fixture 10, includes a base 62 and an attachable coping 64. The base 62 of the abutment 60 has first 66 and second 68 surfaces which are separated by a skirt 70, and a third (or inner) surface 72 that defines an aperture 74 which extends from the first surface 66 to the second surface 68 of the base 62. The first surface 66 of the base 62 of the abutment 60 is complementary to the upper cavity 26 in the head portion 12 of the implant fixture 10. The first surface 66 includes a pair 76, 78 of inverted conical surfaces, an intermediate cylindrical surface 80, and a generally flat end surface 82, but other embodiments may comprise a single inverted conical surface that terminates at the end surface 82 of the base 62 of the abutment 60. Although the intermediate cylindrical surfaces 40, 80 of the implant fixture 10 and abutment 60 are substantially smooth, other embodiments may include complementary polygonal (hexagonal, octagonal, etc.) flat portions, grooves, and so on, which engage one another and prevent rotation of the base 62 of the abutment 60.

As shown in FIG. 2, the second surface 68 has a finite and approximately constant radius of curvature—i.e., has a shape that approximates a section of a sphere—and provides a surface for joining the attachable coping 64 to the base 62 of the abutment 60. The third (inner) surface 72 of the base 62 has a pair of generally cylindrical surfaces 84, 86 that are separated by an annular surface 88 which slopes inward towards a symmetry axis 90 of the base 62 of the abutment 60. The third surface 72 can be substantially smooth, but the embodiment depicted in FIG. 2 employs internal threads 92 along a portion of the cylindrical surface 86 adjacent to the end surface 82 of the base 62 of the abutment 60. As described below, the third surface 72 is configured to receive a connector (see FIG. 4), which joins the base 62 of the abutment 60 to the implant fixture 10. The internal threads 92 retain the connector in the base 62, and aid in removing the abutment 60 from the implant fixture 10. The base 62 can be constructed from any material that is compatible with the implant fixture 10 and the soft tissues within the patient's mouth. Suitable materials include titanium or titanium alloys, gold alloys, and the like, which are machined and milled to the requisite shape.

Continuing with FIG. 2, the abutment 60 also includes an attachable coping 64. Like the neck portion of a conventional abutment, the attachable coping 64 secures the prosthesis to the base 62 of the abutment 60. The attachable coping 64 has an exterior surface 94 that provides a substrate for receiving the prosthesis. As shown in FIG. 2, the exterior surface 94 has a frustum-like shape that when viewed from bottom 96 to top 98 slopes inward towards a longitudinal axis 100. The exterior surface 94 includes first 102 and second 104 openings located at the bottom 96 and top 98 of the attachable coping 64, respectively, and an interior surface 106 that provides a cavity 108 that extends between the first 102 and second 104 openings. The interior surface 106 adjacent to the first opening 102 of the attachable coping 64 defines a depression 110 having a concave shape characterized by a finite and approximately constant radius of curvature. The depression 110 is shaped to slidably engage the second surface 68 of the base 62 of the abutment 60 so that the attachable coping 64 can be joined to the base 62 at a desired angular orientation.

The embodiment shown in FIG. 2 also includes a lateral opening 112, which communicates with the cavity 108 in the attachable coping 64. When the attachable coping 64 is joined to the base 62 of the abutment 60 and the connector is installed in the aperture 74 of the base 62, the lateral opening 112 provides access to the connector. Alternatively or optionally, the second opening 104 of the attachable coping 64 may permit access to the connector following installation of the connector in the base 62 of the abutment 60. In other embodiments, the second opening 104 may include internal threads (not shown) that are sized to engage a threaded connector, which joins the prosthesis to the coping 64. The attachable coping 64 may be constructed from a variety of materials, including plastics that decompose upon heating, titanium and titanium alloys, gold alloys, and the like.

Figure 3:
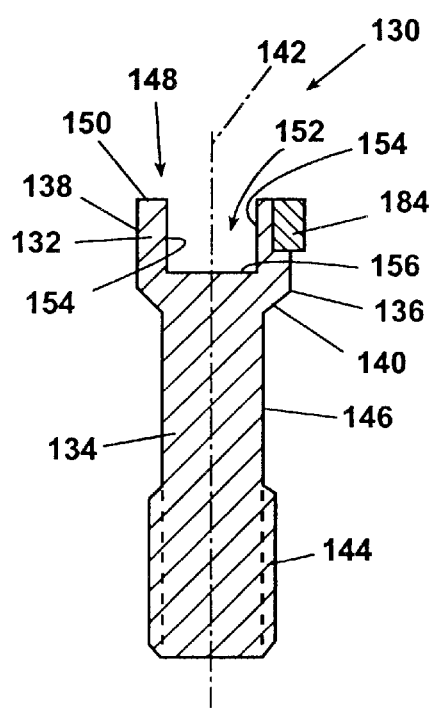
FIG. 3 shows a cross-sectional side view of a connector.

FIG. 3 shows a cross-sectional side view of a connector 130 that secures the abutment 60 to the implant fixture 10. The connector 130 includes a head portion 132 and an adjoining shaft portion 134. The head portion 132 of the connector 130 has an outer lateral surface 136 that is configured to engage the third (or inner) surface 72 of the base 62 of the abutment 60 (FIG. 2). The outer lateral surface 136 thus includes a generally cylindrical surface 138 that intersects an annular surface 140, which slopes inward towards the shaft portion 134 and a symmetry axis 142 of the connector 130. The shaft portion 134 of the connector 130 includes external threads 144 formed along a section of its outer surface 146. The external threads 144 are adapted to engage internal threads 42, 92 formed, respectively, in the lower cavity 28 of the implant fixture 10 (FIG. 1) and along the cylindrical surface 86 that defines part of the aperture 74 extending through the base 62 of the abutment 60. The internal threads 92 in the aperture 74 retain the connector 130 in the base 62 of the abutment 60 when the abutment 60 is not installed on the implant fixture 10.

As can be seen in FIG. 3, the head portion 132 of the connector 130 further includes an end region 148 having a surface 150 that defines a recess 152. The end region 148 of the surface 150 shown in FIG. 3 includes an inner lateral surface 154, which delineates the width of the recess 152, and a bottom surface 156, which marks the depth of the recess 152. The inner lateral surface 154 is sized and dimensioned to receive a tool for driving (e.g., rotating) the connector 130. The inner lateral surface 154 may have polygonal flat portions (e.g., triangular flats) or similar structures formed on it, which provide contact surfaces for a driver tool (e.g., triangle-tipped screwdriver). The connector 130 can be fabricated from any material that is compatible with the abutment 60 and the implant fixture 10 and that has the requisite mechanical properties (e.g., tensile strength, elongation, and modulus). Useful materials include titanium, non-oxidizing alloys, and gold alloys.

Figure 4:
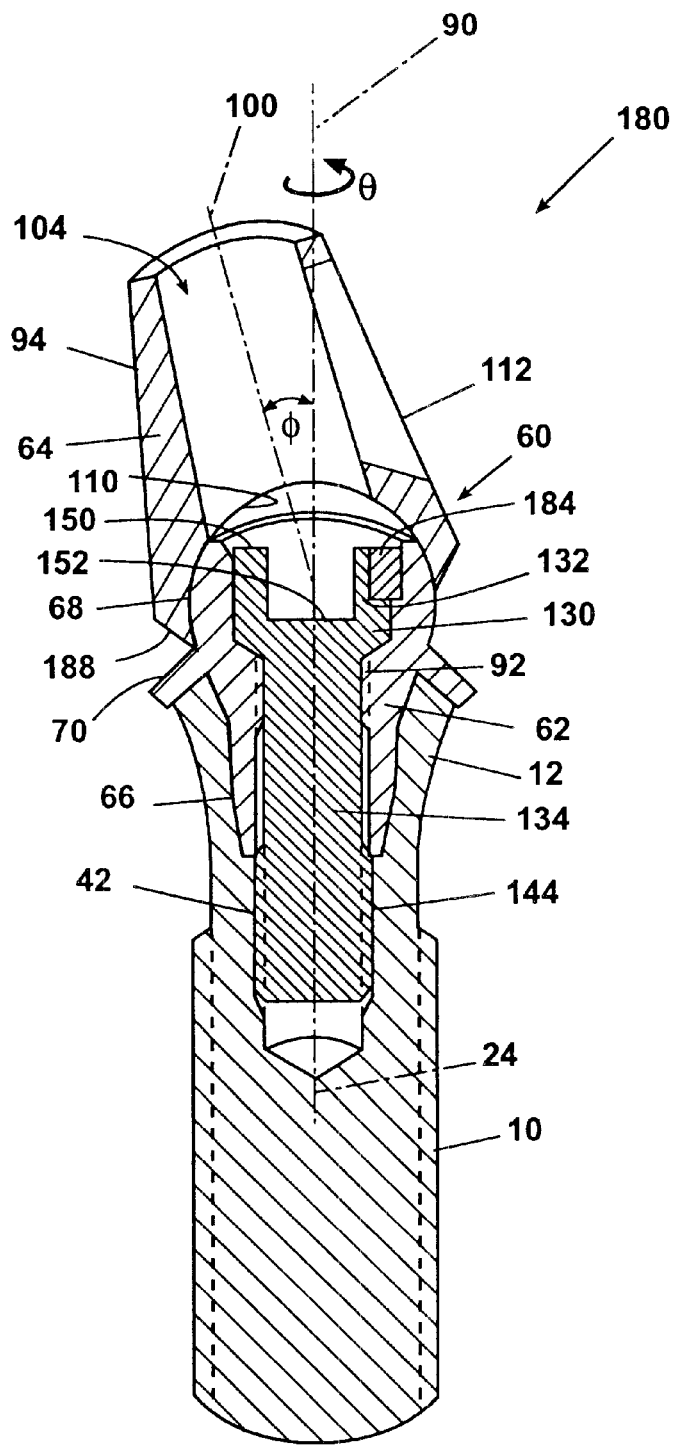
FIG. 4 shows a cross-sectional side view of a dental implant assembly.

FIG. 4 shows a partial cross-sectional side view of a dental implant assembly 180, which includes the implant fixture 10, the abutment 60, and the connector 130 shown in FIG. 1 through FIG. 3, respectively. After the implant fixture has been integrated into the jawbone, the head portion 12 of the implant fixture 10 is exposed (uncovered) by the oral surgeon. The first surface 66 of the base 62 of the abutment 62 is then disposed in the upper cavity 26 of the head portion 12 of the implant fixture 10 so that the respective aperture 74 and hole 20 of the base 62 and the implant fixture 10 are substantially aligned. Next, the connector 130 is placed in the aperture 74 of the base 62 to secure the abutment 60 to the implant fixture 10. A tool, such as a screwdriver, is introduced through either the second opening 104 or the lateral opening 112 in the exterior surface 94 of the attachable coping 64 to engage the recess 152 in the head portion 132 of the connector 130. Twisting or rotating the tool drives the connector 130 into the hole 20 in the implant fixture 10 as the external threads 144 on the shaft portion 134 of the connector 130 engage the internal threads 42 in the lower cavity 28 of the implant fixture 10. Although not shown, the prosthesis joined to the exterior surface 94 of the coping 64 has one or more holes that allow the oral surgeon to access the appropriate openings 104, 112 in the exterior surface 94 of the attachable coping 64. These holes are later filled in.

Figure 5:
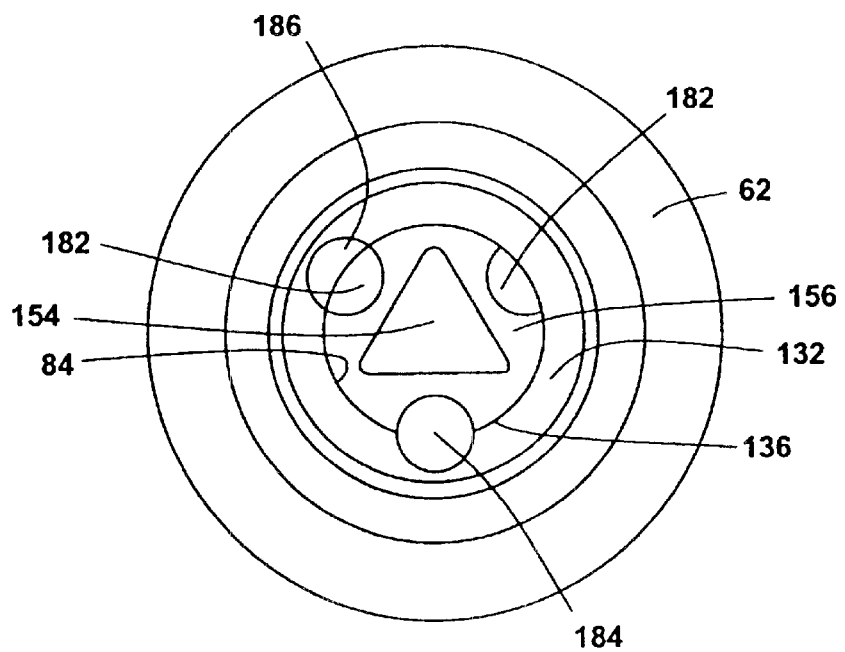
FIG. 5 shows a top view of the dental implant assembly shown in FIG. 4, in which the attachable coping has been removed for clarity.

FIG. 5 is a top view of the dental implant assembly 180 shown in FIG. 4, in which the attachable coping 64 has been removed to show the connector 130 following installation in the aperture 74 of the base 62 of the abutment 60. The head portion 132 of the connector 130 includes a triangular recess 154, which is sized to accommodate a triangle-tipped driver. In addition, the outer lateral surface 136 of the head 132 of the connector 130 includes one or more notches 182 that are adapted to receive locking pins 184 that help prevent rotation of the connector 130 following installation. After the connector 130 has been twisted into the implant fixture 10 to a requisite torque, the oral surgeon drills complementary notches 186 in the cylindrical surface 84 of the base 62 of the abutment 60 adjacent to the head portion 132 of the connector 130. The locking pins 184 are then pressed or rotated into pairs of notches 182, 186, and optionally held in place by applying a settable resin. The locking pins can be fabricated from a thermoplastic material or a metal alloy, such as a gold alloy, which the dental practitioner can easily remove by drilling if it is later necessary to remove the prosthesis and abutment 60 from the implant fixture 10.

Referring again to FIG. 4, the direction or orientation of the attachable coping 64 can be represented by an orientation angle, $\phi$. The orientation angle is formed by the intersection of the longitudinal axis 100 of the attachable coping 64 and the symmetry axis 90, 24 of the base portion 62 of the abutment 60 or of the implant fixture 10. As noted above, the attachable coping 64 includes a depression 110 having a concave shape characterized by a finite and approximately constant radius of curvature. The depression 110 is shaped to slidably engage the second surface 68 of the base 62 of the abutment 60 so that the attachable coping 64 can be joined to the base 62 at the desired orientation angle. As can be seen in FIG. 4, the ball-and-socket joint allows $\phi$ to vary between about zero degrees and about fifty degrees or more for any polar angle, $\theta$. If necessary, a portion 188 of the exterior surface 94 of the attachable coping 64 can be removed to minimize interference between the skirt 70 of the abutment 60 and the attachable coping 64.

Once the implant fixture 10 has been integrated into the jawbone, the dental practitioner threads an impression coping into the implant fixture 10 and makes an impression of the patient's mouth. The impression coping is a type of straight abutment that projects outward from the patient's gum line and precisely locates the position and the orientation of the implant fixture 10 within the patient's mouth. A dental laboratory then prepares a cast of the patient's mouth from the dental impression. Using the cast as a guide, a laboratory technician positions the attachable coping 64 on the base 62 of the abutment 60. If the attachable coping 64 is made of titanium or a titanium alloy, the technician can fix the orientation angle by laser welding the coping 64 to the base 62 of the abutment 60. If the attachable coping 64 is instead made of a heat labile plastic, the technician first fixes the orientation angle by applying wax or resin to attach the coping 64 to the base 62 of the abutment 60. Once the plastic coping 64 has been joined to the base 62, any required alterations of the abutment 60 can be made, such as lengthening the coping 64, tapping the second opening 104 of the coping 64, etc. The technician then invests and casts an angled abutment (coping 64 and base 62) using the "lost wax" technique and appropriate dental materials (e.g. gold alloys).

It may be necessary to remove the prosthesis following installation on the implant fixture 10. In such cases, the dental practitioner accesses the head portion 132 of the connector 130 by drilling into the prosthesis, if necessary. Next, the dental practitioner removes the locking pins 184 (e.g., by drilling), and twists the connector 130 out of the implant fixture 10 using the requisite tool, such as a triangle-tipped screwdriver. As the connector 130 recedes, the external threads 144 along the shaft portion 134 of the connector 130 engage the internal threads 92 on the cylindrical surface 86 that defines a portion of the aperture 74 extending through base 62 of the abutment 60. Because the external threads 144 also engage a section of the internal threads 42 of the hole 20 in the implant fixture 10, the connector 130 exerts a force in the direction of its longitudinal axis 142 against the base 62 of the abutment 60. The force pushes the base 62 out of the upper cavity 26 of the implant fixture 10.

Figure 6:
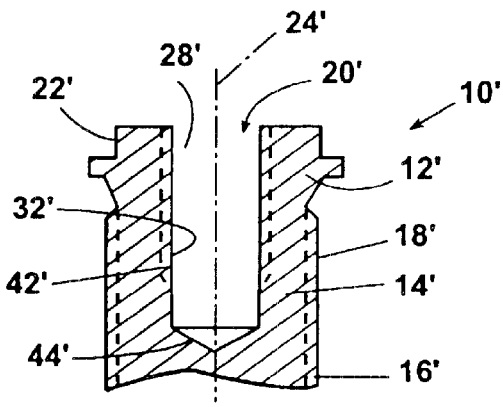
FIG. 6 shows a cross-sectional side view of a second embodiment of an implant fixture.
Figure 7:
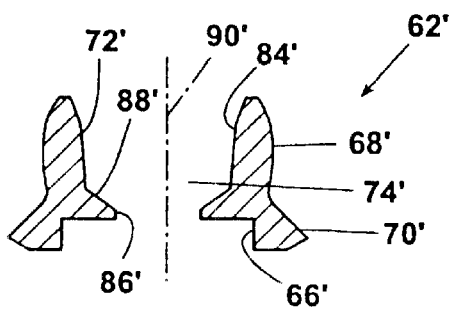
FIG. 7 shows a partial cross-sectional side view of a base portion of an abutment adapted for use with the implant fixture shown in FIG. 6.

FIG. 6 and FIG. 7 show, respectively, cross-sectional side views of second embodiments of an implant fixture 10' and a base portion 62' of an abutment, respectively. Like the embodiment shown in FIG. 1, the implant fixture 10' is also a root-form implant fixture and includes a head portion 12' and an adjoining root portion 14'. In addition, the implant fixture 10' has a generally cylindrical shape and has external threads 16' formed along a section of an exterior surface 18' of the elongated root portion 14'. The implant fixture 10' includes a longitudinal bore or hole 20', which extends from an upper exterior surface 22' of the head portion 12' into the elongated root portion 14' of the implant fixture 10'. The hole 20', which has a centerline substantially coincident with a symmetry axis 24' of the implant fixture 10', includes a cavity 28' defined by an interior surface 32', which is adapted to receive the connector 130 (FIG. 2). The interior surface 32' has a cylindrical shape, and includes internal threads 42' that extend from the head portion 12' to a region adjacent to the bottom 44' of the hole 20'. The exterior surface 22' of the head portion 12 of the implant fixture 10' has a polygonal (e.g., hexagonal) shape, which is adapted to receive a tool (e.g., hex head socket driver) for rotating the implant fixture 10' into the jawbone.

As can be seen in FIG. 7, the base 62' of the abutment has first 66' and second 68' surfaces which are separated by a skirt 70', and a third (or inner) surface 72' that defines an aperture 74' which extends from the first surface 66' to the second surface 68' of the base 62'. The first surface 66' of the base 62' of the abutment 60' is complementary to the exterior surface 22' of the head portion 12' of the implant fixture 10' shown in FIG. 6. The second surface 68' has a finite and approximately constant radius of curvature—i.e., has a shape that approximates a section of a sphere—and provides a surface for joining the attachable coping 64' (FIG. 2) to the base 62' of the abutment 60'. The third (inner) surface 72' of the base 62' has a pair of generally cylindrical surfaces 84', 86' that are separated by an annular surface 88' which slopes inward towards a symmetry axis 90' of the base 62' of the abutment 60'. As described above, the third surface 72' is configured to receive the connector 130 (FIG. 3), which joins the base 62' of the abutment 60' to the implant fixture 10'.

The above description is intended to be illustrative and not restrictive. Many embodiments and many applications besides the examples provided would be apparent to those of skill in the art upon reading the above description. The scope of the invention should therefore be determined, not with reference to the above description, but should instead be determined with reference to the appended claims, along with the full scope of equivalents to which such claims are entitled. The disclosures of all articles and references, including patent applications and publications, are hereby incorporated by reference in their entirety for all purposes.

What is claimed is:

1. An assembly for securing a permanent prosthesis to an implant fixture, the assembly comprising:

an abutment comprised of a base and an attachable coping, the base having a first surface that is complementary to a head portion of the implant fixture, a second surface having a shape that approximates a section of a sphere, and a third surface that defines an aperture extending between the first and second surfaces of the base, the attachable coping having an exterior surface and a depression formed at one end of the attachable coping, the exterior surface adapted to receive the permanent prosthesis and the depression shaped to slidably engage the second surface of the base so that the attachable coping can be joined to the base at a desired angular orientation; and a connector having a head portion and a shaft portion adjoining the head portion, the head portion of the connector defining one end of the connector and shaped to engage the third surface of the base of the abutment, and the shaft portion of the connector having external threads adapted to engage internal threads in a lower cavity of the implant fixture so that the one end of the connector lies substantially within the aperture of the abutment following assembly.

2. The assembly of claim 1, wherein the head portion of the connector has a recess that is configured to receive a tool for driving the connector into the hole in the implant fixture.

3. The assembly of claim 2, wherein the recess in the head portion of the connector has a polygonal shape.

4. The assembly of claim 2, wherein the recess in the head portion of the connector has a triangular shape.

5. An assembly for securing a permanent prosthesis to an implant fixture, the assembly comprising:

an abutment comprised of a base and an attachable coping, the base having a first surface that is complementary to a head portion of the implant fixture, a second surface having a shape that approximates a section of a sphere, and a third surface that defines an aperture extending between the first and second surfaces of the base, the attachable coping having an exterior surface and a depression formed at one end of the attachable coping, the exterior surface adapted to receive the permanent prosthesis and the depression shaped to slidably engage the second surface of the base so that the attachable coping can be joined to the base at a desired angular orientation; and a connector having a head portion and a shaft portion adjoining the head portion, the head portion of the connector defining one end of the connector and shaped to engage the third surface of the base of the abutment, and the shaft portion of the connector having external threads adapted to engage internal threads in a hole in the implant fixture so that the one end of the connector lies substantially within the aperture of the abutment following assembly;

wherein the base of the abutment has internal threads along a section of the third surface, the internal threads adapted to engage the external threads of the shaft portion of the connector.

6. An assembly for securing a permanent prosthesis to an implant fixture, the assembly comprising:

an abutment comprised of a base and an attachable coping, the base having a first surface that is complementary to a head portion of the implant fixture, a second surface having a shape that approximates a section of a sphere, and a third surface that defines an aperture extending between the first and second surfaces of the base, the attachable coping having an exterior surface and a depression formed at one end of the attachable coping, the exterior surface adapted to receive the permanent prosthesis and the depression shaped to slidably engage the second surface of the base so that the attachable coping can be joined to the base at a desired angular orientation;

a connector having a head portion and a shaft portion adjoining the head portion, the head portion of the connector defining one end of the connector and shaped to engage the third surface of the base of the abutment, and the shaft portion of the connector having external threads adapted to engage internal threads in a hole in the implant fixture so that the one end of the connector lies substantially within the aperture of the abutment following assembly; and a locking pin disposed in adjacent notches formed in the head portion of the connector and the base of the abutment.

7. An assembly for securing a permanent prosthesis to an implant fixture, the assembly comprising:

an abutment comprised of a base and an attachable coping, the base having a first surface that is complementary to a head portion of the implant fixture, a second surface having a shape that approximates a section of a sphere, and a third surface that defines an aperture extending between the first and second surfaces of the base, the attachable coping having an exterior surface and a depression formed at one end of the attachable coping, the exterior surface adapted to receive the permanent prosthesis and the depression shaped to slidably engage the second surface of the base so that the attachable coping can be joined to the base at a desired angular orientation;

a connector having a head portion and a shaft portion adjoining the head portion, the head portion of the connector shaped to engage the third surface of the base of the abutment, and the shaft portion of the connector having external threads adapted to engage internal threads in a hole in the implant fixture; and a locking pin disposed in adjacent notches formed in the head portion of the connector and the base of the abutment.

8. An assembly for securing a permanent prosthesis to an implant fixture, the assembly comprising:

an abutment comprised of a base and an attachable coping, the base having a first surface that is complementary to a head portion of the implant fixture, a second surface having a shape that approximates a section of a sphere, and a third surface that defines an aperture extending between the first and second surfaces of the base, the attachable coping having an exterior surface and a depression formed at one end of the attachable coping, the exterior surface adapted to receive the permanent prosthesis and the depression shaped to slidably engage the second surface of the base so that the attachable coping can be joined to the base at a desired angular orientation; and a connector having a head portion and a shaft portion adjoining the head portion, the head portion of the connector shaped to engage the third surface of the base of the abutment, and the shaft portion of the connector having external threads adapted to engage internal threads in a hole in the implant fixture and along a section of the third surface of the abutment.

9. A dental implant assembly comprising:

an implant fixture having a head portion, an elongated root portion adjoining the head portion, and a hole extending from the head portion into the elongated root portion, the implant fixture having internal threads in at least a lower segment of the hole;

an abutment comprised of a base and an attachable coping, the base having a first surface that is complementary to the head portion of the implant fixture, a second surface having a shape that approximates a section of a sphere, and a third surface that defines an aperture extending between the first and second surfaces of the base, the attachable coping having an exterior surface and a depression formed at one end of the attachable coping, the exterior surface adapted to receive the permanent prosthesis and the depression shaped to slidably engage the second surface of the base so that the attachable coping can be joined to the base at a desired angular orientation; and a connector having a head portion and a shaft portion adjoining the head portion, the head portion of the connector defining one end of the connector and shaped to engage the third surface of the base of the abutment, and the shaft portion of the connector having external threads adapted to engage the internal threads in the lower segment of hole so that the one end of the connector lies substantially within the aperture of the abutment following assembly.

* * * * *